United States Patent

Souma

[11] Patent Number: 5,135,003
[45] Date of Patent: Aug. 4, 1992

[54] AUTOMATIC SPHYGMOMANOMETER

[75] Inventor: Takahiro Souma, Kanagawa, Japan

[73] Assignee: Terumo Kabushiki Kaisha, Tokyo, Japan

[21] Appl. No.: 460,110

[22] PCT Filed: Aug. 11, 1988

[86] PCT No.: PCT/JP88/00801
  § 371 Date: Feb. 9, 1990
  § 102(e) Date: Feb. 9, 1990

[87] PCT Pub. No.: WO89/01310
  PCT Pub. Date: Feb. 23, 1989

[30] Foreign Application Priority Data

Aug. 11, 1987 [JP] Japan ................................. 62-199155
Aug. 11, 1987 [JP] Japan ................................. 62-199156

[51] Int. Cl.$^5$ .............................................. A61B 5/02
[52] U.S. Cl. ..................................... 128/680; 128/682
[58] Field of Search ................ 128/672, 677, 680–685, 128/687, 691

[56] References Cited

U.S. PATENT DOCUMENTS 4,026,277  5/1977  Toda ..................................... 128/680
4,484,584  11/1984  Uemera ............................... 128/680
4,546,775  10/1985  Medero ............................... 128/680

FOREIGN PATENT DOCUMENTS 0350076  1/1990  European Pat. Off. ............ 128/680
2069704A  8/1981  United Kingdom .
2165052A  4/1986  United Kingdom .
84/01499  4/1984  World Int. Prop. O. .

Primary Examiner—Kyle L. Howell
Assistant Examiner—Robert L. Nasser, Jr.
Attorney, Agent, or Firm—Staas & Halsey

[57] ABSTRACT

An automatic sphygmomanometer for measuring the blood pressure of a subject based on Korotkoff sounds is adapted to analyze the transition of the pulse signal amplitude of a detected cuff pressure signal, set a range in which systolic blood pressure of the subject is capable of residing and a range in which diastolic blood pressure of the subject is capable of residing, and evaluate, based on appearance and disappearance of the Korotkoff sounds, whether the blood pressures that have determined reside in the set ranges. Preferably, the sphygmomanometer is provided with two amplifying-/filtering circuits and two discriminating circuits using threshold values suited to each of the frequency characteristics of Korotkoff sound signals in the vicinity of the systolic and diastolic blood pressures. This improves the precision with which each blood pressure is determined. Preferably, the amplified/filtered signals and threshold signals of the two sets of circuits are capable of being externally extracted, and these signals are capable of being externally adjusted so that the electronic sphygmomanometer may be calibrated by making joint use of an auscultation method.

9 Claims, 14 Drawing Sheets

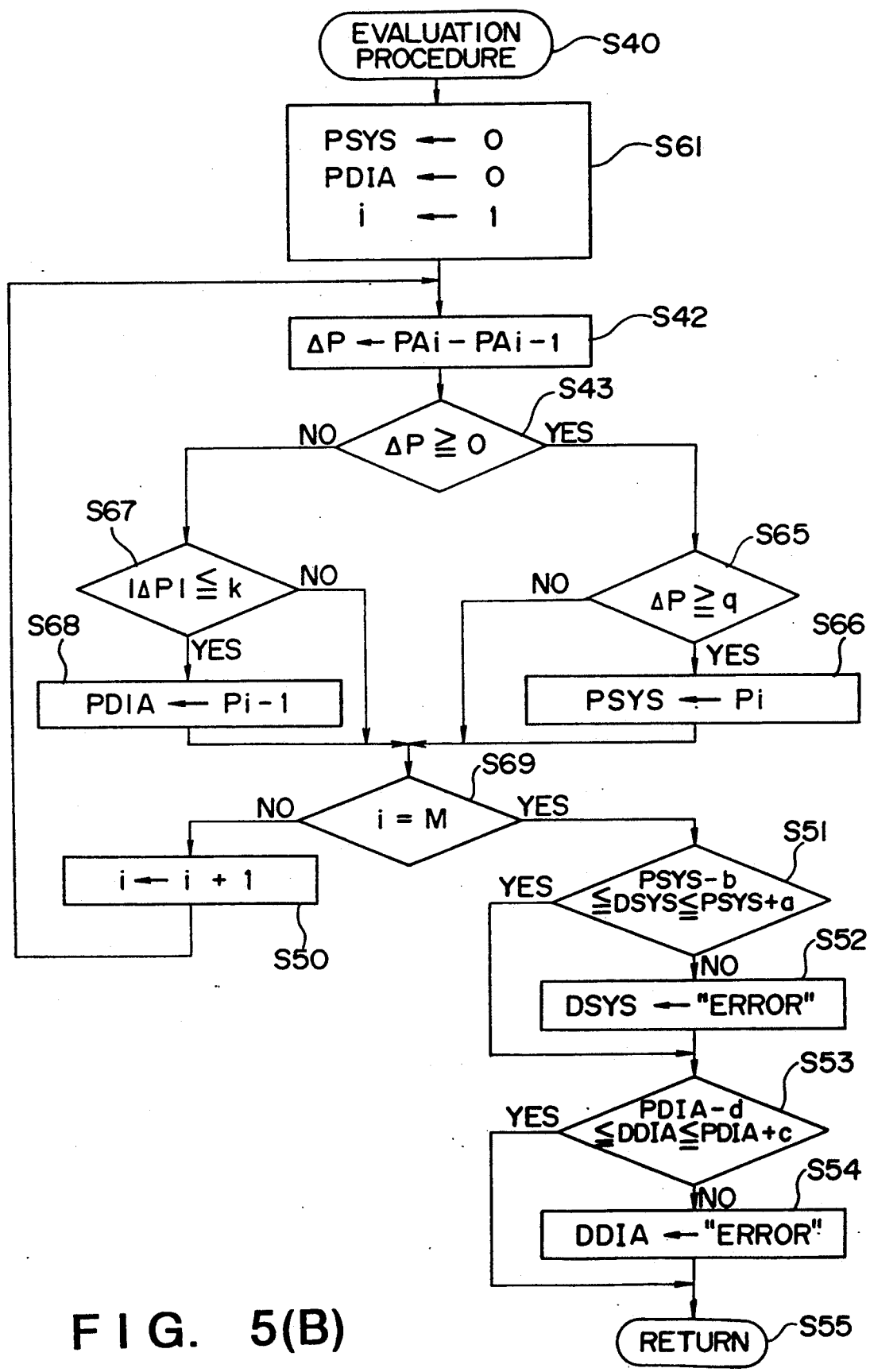
F I G. 5(B)

AUTOMATIC SPHYGMOMANOMETER

BACKGROUND OF THE INVENTION

1. Field of the Invention

This invention relates to an automatic sphygmomanometer and, more particularly, to an automatic sphygmomanometer for measuring the systolic and diastolic blood pressures of a subject undergoing measurement by automatically identifying the appearance and disappearance of a Korotkoff sound signal.

2. Description of the Related Art

Fundamentally speaking, the measurement of blood pressure often relies upon audible recognition of Korotkoff sounds by the individual (such as a physician) taking the measurement. For this reason, even digital sphygmomanometers adapted to automatically recognize the appearance and disappearance of the Korotkoff sound signal are widely available. However, since the Korotkoff sounds are extremely low in volume, detection is easily influenced by noise arising from motion of the body and rubbing sounds produced by the cuff and tube, as a result of which systolic blood pressure and diastolic blood pressure are often perceived incorrectly. Accordingly, an expedient available in the prior art relies upon generating a pulse (heartbeat) signal in synchronization with the Korotkoff sound signal, wherein a noise gate is applied by the pulse signal to make the Korotkoff sound signal more resistant to noise. However, since this synchronized relationship is not always constant, as in cases where the pulse is irregular or the subject undergoing measurement is hypertensive, misrecognition due to a shift in synchronization often occurs. Moreover, since a pseudo-Korotkoff sound signal and pseudo-pulse signal are generated simultaneously, as when the body moves, the noise gate is rendered meaningless in terms of improving the anti-noise property.

Furthermore, the result of recognition performed by an automatic sphygmomanometer of this type and the result of recognition performed through auscultation by the person taking the measurement do not always coincide. Accordingly, it is preferred from a medical point of view that even an automatic sphygmomanometer of this kind be capable of calibration based on auscultation. In the conventional sphygmomanometer, however, the gain of an amplifier (filter amplifier) for the Korotkoff sound signal or the threshold level for recognizing the Korotkoff sound signal is fixed. Once the sphygmomanometer has been manufactured, therefore, only the quality thereof can be verified by auscultation.

Though amplifier gain, threshold level and filter constant are quantities which can be adjusted, in the prior art the signals necessary for these adjustments cannot be extracted for external use. This makes it difficult to perform the adjustments at the time of use, and confirmation by auscultation and adjustment based on sensation need to be repeated a number of times.

In addition, since only a single processing circuit for amplifying and filtering the Korotkoff sound signal is provided, it is impossible to perform separate adjustments for determining systolic blood pressure and diastolic blood pressure.

SUMMARY OF THE INVENTION

The present invention eliminates the foregoing drawbacks of the prior art and its object is to provide a highly reliable automatic sphygmomanometer by effectively exploiting the relationship between the transition of a pulse signal and the systolic and diastolic blood pressures of the subject undergoing measurement.

Another object of the present invention is to provide an automatic sphygmomanometer capable of measuring systolic and diastolic blood pressures accurately.

Still another object of the present invention is to provide an automatic sphygmomanometer in which systolic and diastolic blood pressures can be calibrated with ease.

In order to attain the foregoing objects, the automatic sphygmomanometer of the present invention comprises cuff pressure detecting means for detecting cuff pressure and outputting a cuff pressure signal, Korotkoff sound detecting means for detecting Korotkoff sounds and outputting a Korotkoff sound signal, Korotkoff sound signal processing means for performing amplifying and filtering processing based on the detected Korotkoff sound signals and comparing the Korotkoff sound signals that have been processed with a predetermined threshold value, thereby extracting Korotkoff sound signals which exceed the predetermined threshold value, blood pressure determining means for determining systolic blood pressure and diastolic blood pressure based on the extracted Korotkoff sound signals, range setting means for setting, based on a transition of a pulse signal component of the detected cuff pressure signal, a range in which systolic blood pressure of a subject undergoing measurement is capable of residing and a range in which diastolic blood pressure of the subject is capable of residing, evaluating means for determining whether the blood pressures determined by the blood pressure determining means reside in the ranges set by the range setting means, and display means for displaying information indicative of the blood pressures determined by the blood pressure determining means and information indicative of the determination made by the evaluating means.

In a preferred embodiment, the range setting means sets, as the range in which the systolic blood pressure is capable of residing, a predetermined range which includes cuff pressure that prevails at the moment a pulse signal, which is equivalent to the maximum amplitude of the pulse signal component multiplied by n ($0<n<1$), appears at the beginning or end of a measurement phase, and sets, as the range in which the diastolic blood pressure is capable of residing, a predetermined range which includes cuff pressure that prevails at the moment a pulse signal, which is equivalent to the maximum amplitude of the pulse signal component multiplied by m ($0<m<1$), appears at the end or beginning of a measurement phase, these settings being made in conformity with a cuff deflation measurement or cuff inflation measurement sequence.

In a preferred embodiment, the range setting means sets, as the range in which the systolic blood pressure is capable of residing, a predetermined range which includes cuff pressure that prevails at the moment signal amplitudes of consecutive pulse signal components exhibit more than a predetermined rate of increase at the beginning of a measurement phase or less than a predetermined rate of decrease at the end of a measurement phase, and sets, as the range in which the diastolic blood pressure is capable of residing, a predetermined range which includes cuff pressure that prevails at the moment signal amplitudes of consecutive pulse signal components exhibit less than a predetermined rate of decrease at the end of a measurement phase or more than a predetermined rate of increase at the beginning of a measurement phase, these settings being made in conformity with a cuff deflation measurement or cuff inflation measurement sequence.

In a preferred embodiment, the display means adds flashing information to information indicative of blood pressure determined to be unacceptable by the evaluating means.

In a preferred embodiment, the display means displays an error message instead of information indicative of blood pressure determined to be unacceptable by the evaluating means.

Further, in order to attain the foregoing objects, the automatic sphygmomanometer of the present invention comprises Korotkoff sound signal processing means for performing amplifying and filtering processing based on detected Korotkoff sound signals and comparing the Korotkoff sound signals that have been processed with a predetermined threshold value, thereby extracting Korotkoff sound signals which exceed the predetermined threshold value, blood pressure determining means for determining systolic blood pressure and diastolic blood pressure based on the extracted Korotkoff sound signals, signal extracting means for externally extracting the Korotkoff sound signals that have been processed or a signal indicative of the predetermined threshold value, and adjusting means capable of externally adjusting the amplitude of the Korotkoff sound signals that have been processed, the predetermined threshold value or a filter constant.

In a preferred embodiment, the Korotkoff sound signal processing means comprises first filter means for passing Korotkoff sound signals in the vicinity of systolic blood pressure, first comparator means for comparing the Korotkoff sound signals passed by the first filter means with a first predetermined threshold value, second filter means for passing Korotkoff sound signals in the vicinity of diastolic blood pressure, and second comparator means for comparing the Korotkoff sound signals passed by the second filter means with a second predetermined threshold value.

In a preferred embodiment, the blood pressure determining means determines systolic blood pressure to be that blood pressure which prevails at the moment Korotkoff sound signals extracted by the first comparator means appear or disappear, and determines diastolic blood pressure to be that blood pressure which prevails at the moment Korotkoff sound signals extracted by the second comparator means disappear or appear, these determinations being made in conformity with a cuff deflation measurement or cuff inflation measurement sequence.

BRIEF DESCRIPTION OF THE DRAWINGS

FIG. 5(B) is a flowchart of another evaluation procedure performed by the MPU 9;

DESCRIPTION OF THE PREFERRED EMBODIMENT

Embodiments according to the present invention will now be described in detail in accordance with the accompanying drawings.

Measurement Method 1

There is a difference between the frequency spectrum of a Korotkoff sound signal at the moment (in the vicinity of systolic blood pressure) arterial flow in the upper arm begins from the ischemic state and the frequency spectrum of a Korotkoff sound signal at the moment (in the vicinity of diastolic blood pressure) the arterial flow in the upper arm substantially approximates the normal flow state. The characterizing feature of the measurement method 1 utilizes this property and resides in subjecting these Korotkoff sound signals to signal processing separately to make possible more precise, accurate measurement of blood pressure.

Figure 7A:
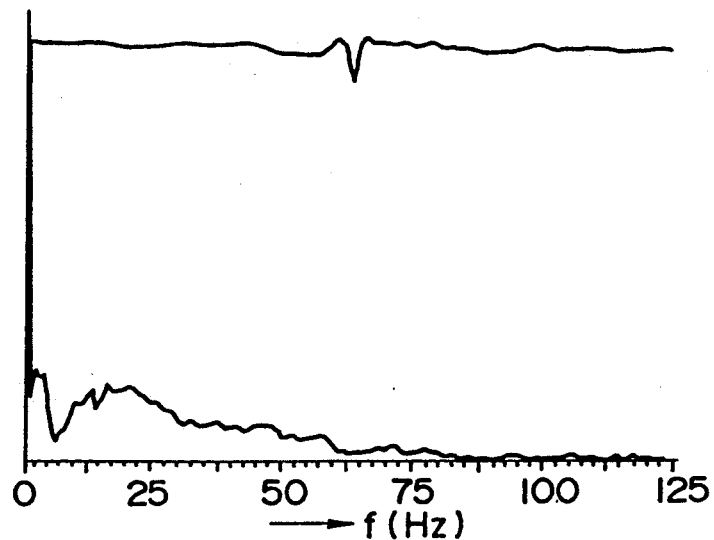
FIGS. 7(A)-7(C) are diagrams showing Korotkoff sound signals at principal points and the frequency spectrums thereof.
Figure 7B:
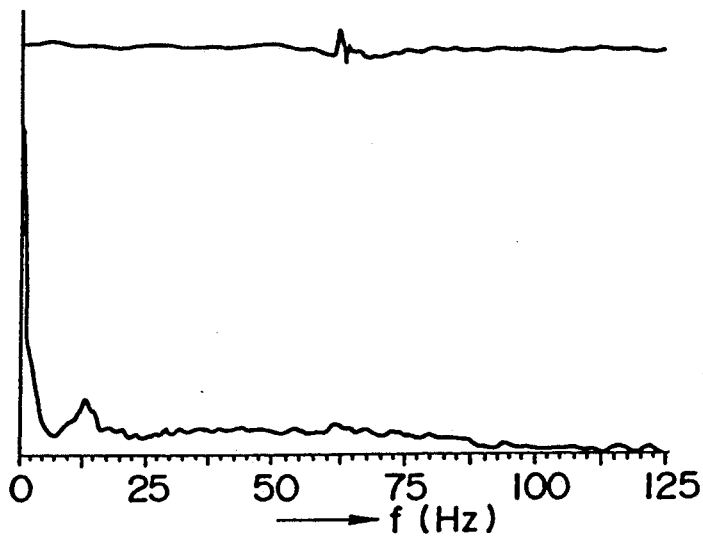
Figure 7C:
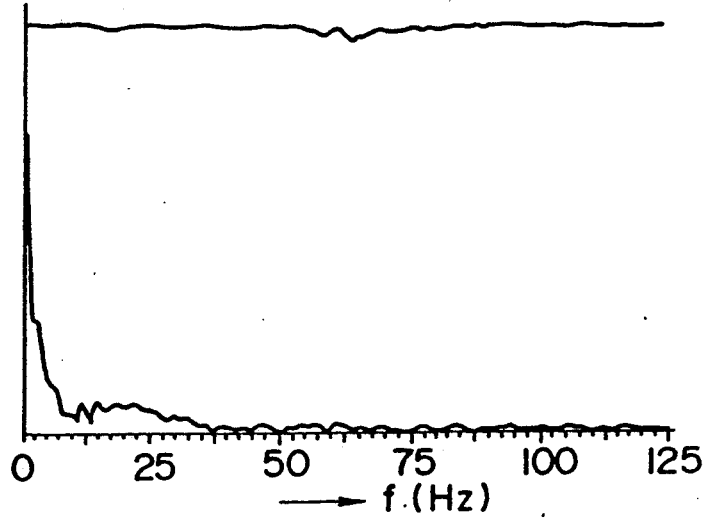

FIGS. 7(A) through 7(C) are diagrams showing Korotkoff sound signals at principal points as well as the frequency spectra of these signals. FIG. 7(A) illustrates a Korotkoff sound signal at the moment systolic blood pressure SYS is determined, 7(B) a Korotkoff sound signal at the moment diastolic blood pressure DIA is determined, and 7(C) a Korotkoff sound signal at the next moment when diastolic blood pressure DIA is recognized based on the signal of FIG. 7(B). As will be evident from observing FIG. 7(A), the principal components of the Korotkoff sound signal in the vicinity of systolic blood pressure are distributed over a range of 10–60 Hz. On the other hand, as will be evident from observing FIG. 7(B), the principal components of the Korotkoff sound signal in the vicinity of diastolic blood pressure are distributed over a range of 10–80 Hz. In the vicinity of diastolic blood pressure, as is apparent, main components are contained even over a range of 60–80 Hz in terms of the ratio of the spectral distribution and therefore cannot be neglected. Accordingly, detected Korotkoff sound signals are processed by two filtering circuits applicable to the Korotkoff sound signals at both points in time. As will be apparent from observing FIG. 7(C), almost no components in the 40–80 Hz range are present at the moment the Korotkoff sound signal vanishes (the moment at which diastolic blood pressure is recognized). Accordingly, if a Korotkoff sound signal in the vicinity of diastolic blood pressure is passed through a filter circuit having 10-80 Hz band-pass characteristic, then the discrepancy between the Korotkoff sound signal waveform of FIG. 7(B) and the Korotkoff sound signal waveform of FIG. 7(C) will appear clearly in the output of the filter circuit, thus making it possible to accurately determine the moment at which the Korotkoff sound signal vanishes.

Figure 1:
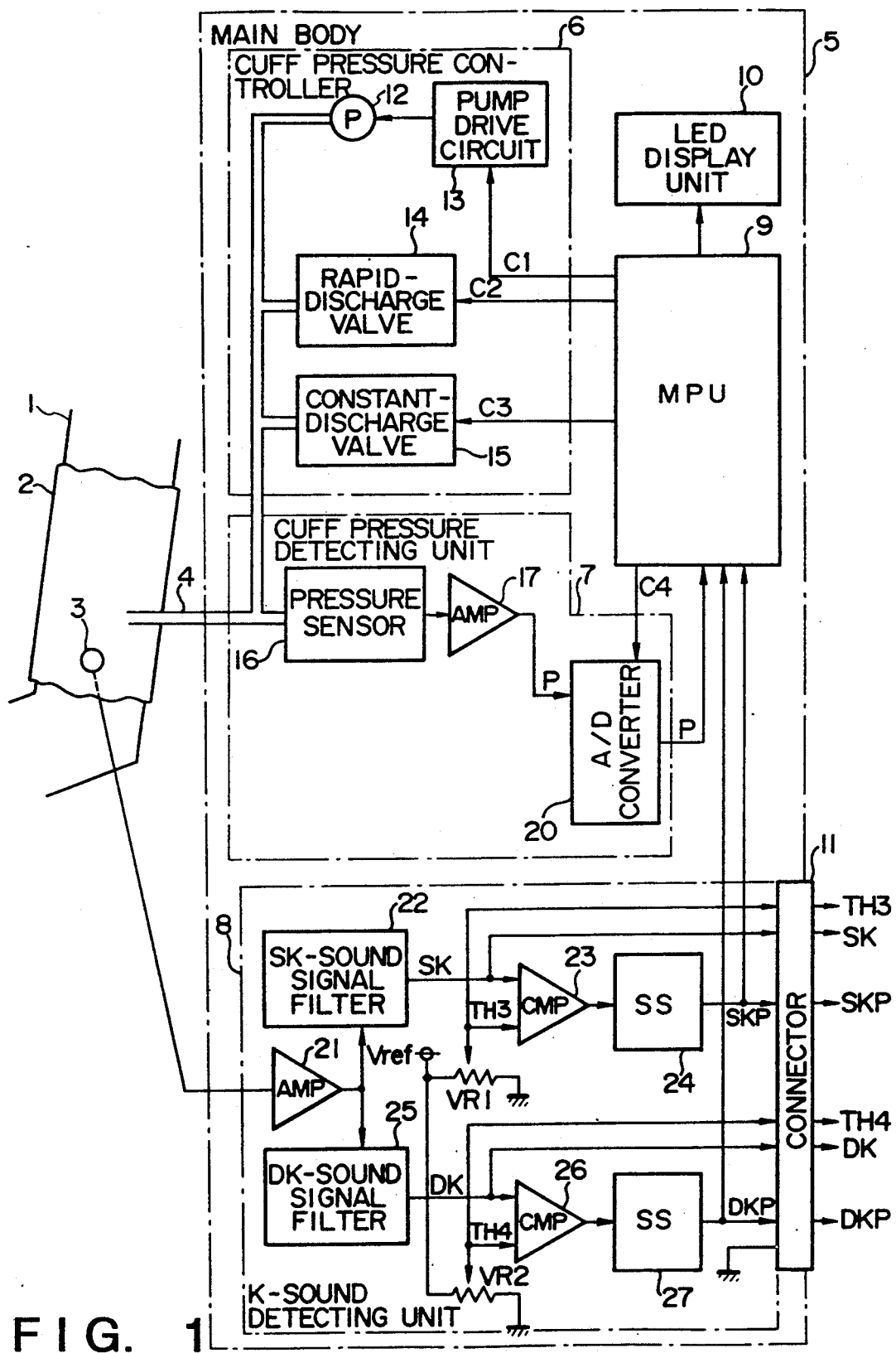
FIG. 1 is a block diagram of an automatic sphygmomanometer using a measurement method 1 according to the present invention.

FIG. 1 is a block diagram showing an automatic sphygmomanometer using measurement method 1 according to the present invention. In FIG. 1, numeral 1 denotes the upper arm of a subject undergoing measurement, 2 a cuff wound about the upper arm 1, 3 a microphone (a capacitor microphone, displacement-type piezoelectric element, etc.) for detecting Korotkoff sounds, 4 a rubber pipe forming the supply/discharge passage of the cuff 2, 5 the main body of an automatic sphygmomanometer using measurement method 1, 6 a cuff pressure controller for controlling cuff pressure, 7 a cuff pressure detecting unit for detecting cuff pressure, 8 a K-sound detector for detecting Korotkoff sounds, 9 a microprocessing unit (MPU) for determining systolic blood pressure and diastolic blood pressure and for performing main control of the automatic sphygmomanometer, 10 a liquid crystal (LED) display for displaying systolic blood pressure, diastolic blood pressure and the like, and 11 a connector for externally extracting signals necessary for adjusting (calibrating) the K-sound detector 8.

In the cuff pressure controller 6, numeral 12 denotes an inflating pump for inflating the cuff 2, 13 a pump drive circuit for driving the inflating pump 12 in response to a control signal C1 from the MPU 9, 14 a rapid-discharge valve for rapidly deflating the cuff in response to a control signal C2 from the MPU 9, and 15 a constant-discharge valve for discharging the cuff at a fixed rate (e.g., 2-4 mmHg/sec) in response to a control signal C3 from the MPU 9.

In the cuff pressure detecting unit 7, numeral 16 denotes a pressure sensor for sensing cuff pressure, 17 an amplifier (AMP) for amplifying the cuff pressure detection signal to output a cuff pressure signal P, and 20 an A/D converter for sampling the cuff pressure signal P and converting the same into a digital signal in response to a control signal C4 from the MPU 9.

In the K-sound detector 8, numeral 21 denotes an AMP for amplifying Korotkoff sounds or a similar detection signal indicating the sound of body surface displacement, 22 an SK-sound filter, which has a band-pass characteristic (e.g., 10-60 Hz) suited to a Korotkoff sound signal produced in the vicinity of the systolic blood pressure of the subject undergoing measurement, for outputting a Korotkoff sound signal SK, 23 a comparator (CMP) which, by comparing the Korotkoff sound signal SK with a predetermined threshold value TH3, outputs Korotkoff sound signals SK which exceed the threshold value TH3, and 24 a single-shot circuit (SS) which, when the Korotkoff sound signal SK exceeds the predetermined threshold value TH3, synchronously outputs a Korotkoff sound pulse signal SKP having a predetermined pulse width. Further, numeral 25 denotes a DK sound signal filter, which has a band-pass characteristic (e.g., 40-100 Hz) suited to a Korotkoff sound signal produced in the vicinity of the diastolic blood pressure of the subject undergoing measurement, for outputting a Korotkoff sound signal DK, 26 a comparator (CMP) which, by comparing the Korotkoff sound signal DK with a predetermined threshold value TH4, outputs Korotkoff sound signals DK which exceed the threshold value TH4, and 27 a single-shot circuit (SS) which, when the Korotkoff sound signal DK exceeds the predetermined threshold value TH4, synchronously outputs a Korotkoff sound pulse signal DKP having a predetermined pulse width.

Figure 2:
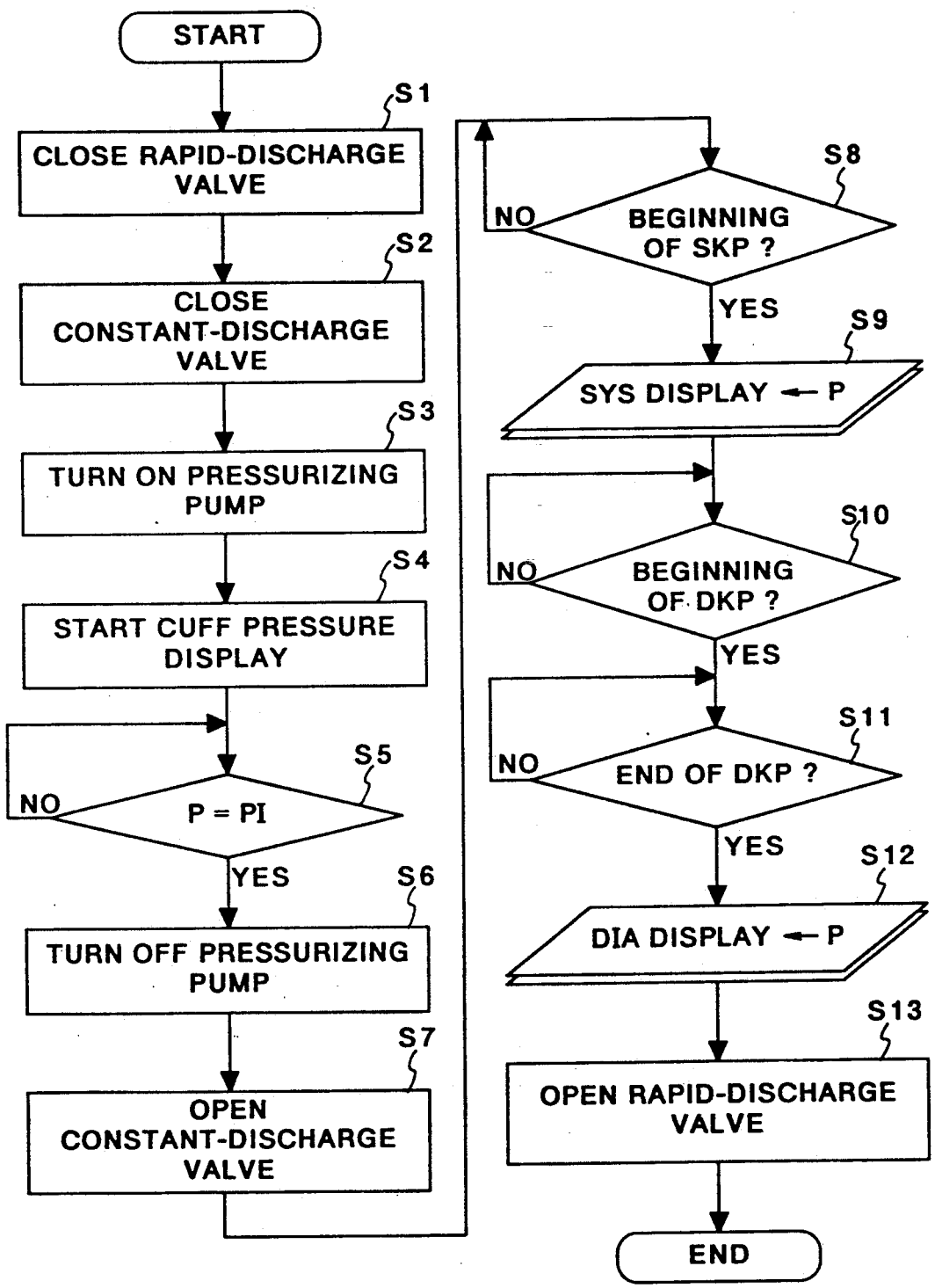
FIG. 2 is a flowchart showing a measurement control procedure of the measurement method 1 performed by an MPU 9.
Figure 6:
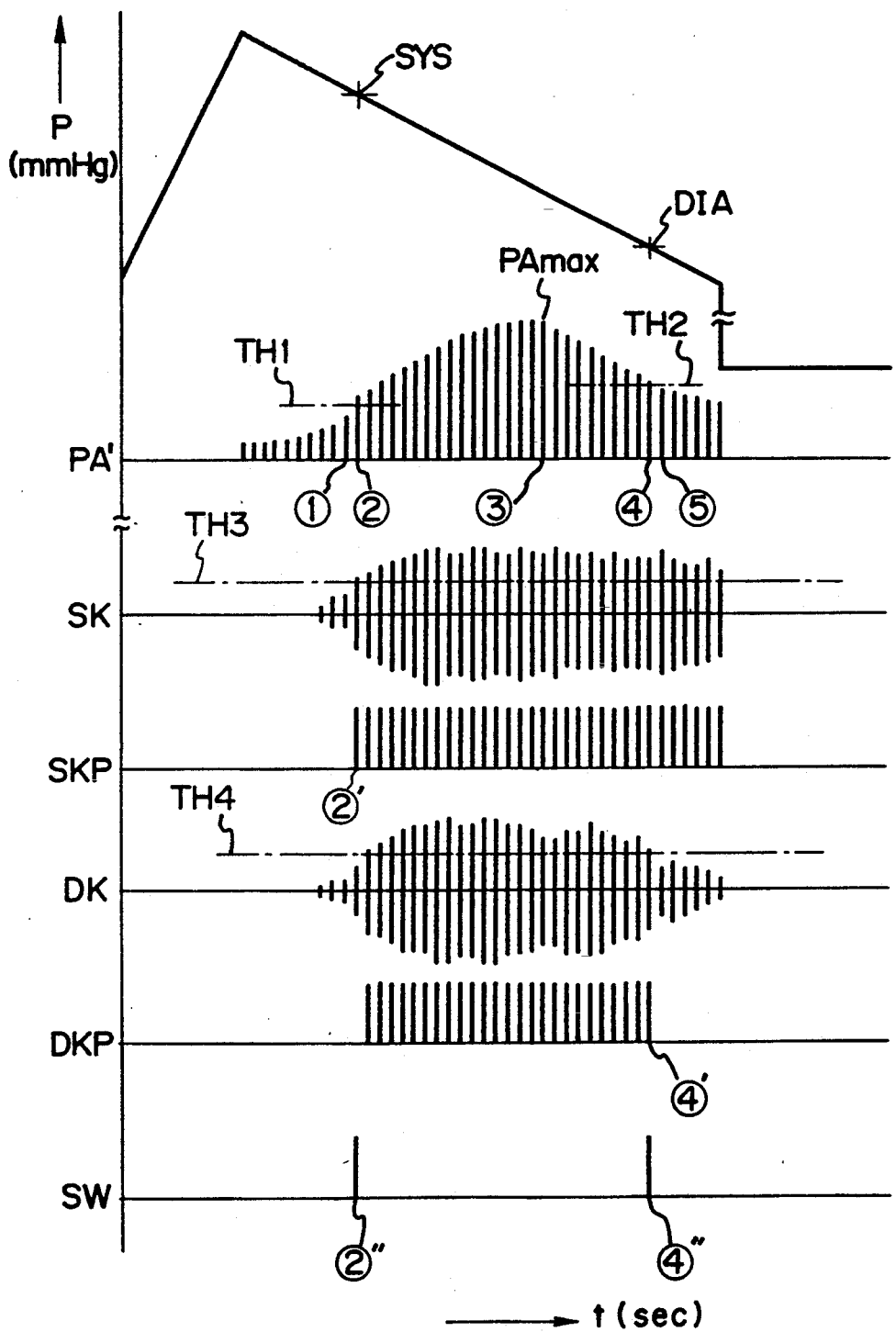
FIG. 6 is an operation timing chart of the automatic sphygmomanometer using a measurement method 2 according to the present invention.

FIG. 2 is a flowchart showing a measurement control procedure of the measurement method 1 performed by the MPU 9, and FIG. 6 is an operation timing chart for part of the procedure. Cuff pressure is assumed to be initially zero in FIG. 2. The rapid-discharge valve 14 is closed at step S1, the constant-discharge valve 15 is closed at step S2, and the inflating pump 12 is turned on at step S3. Then the cuff 2 begins to inflate. At step S4, the MPU 9 starts control to periodically output the control signal C4, read the cuff pressure P and display the cuff pressure P on the LED display device 10. This makes it possible for the subject undergoing measurement to ascertain the transition in cuff pressure. At step S5, the system waits for the cuff pressure P to attain a predetermined value PI (e.g., a predetermined value of 150-200 mmHg) sufficient to stop arterial pulsation of the upper arm. When the predetermined value PI is attained, the inflating pump 12 is turned OFF at step S6. This ends the inflating cycle. The constant-discharge valve 15 is opened at step S7 to begin deflation of the cuff at a constant rate (2-4 mmHg/sec) so that a transition is made to blood pressure measurement cycle. The system waits for the start of the Korotkoff sound pulse signal SKP (the appearance of Korotkoff sounds) at step S8.

When cuff pressure begins decreasing from the ischemic state in FIG. 6, cuff pressure is overcome and arterial flow in the upper arm commences at a certain time, upon which Korotkoff sounds appear. Since the SK-sound filter 22 discriminates (passes) the Korotkoff sound signals at this time, the Korotkoff sound signals passed by the SK sound filter are little affected by noise. As a result, occurrence of the Korotkoff sounds is detected with excellent reliability. The CMP 23 compares the Korotkoff sound signal SK with the threshold value TH3 and makes the SS 24 to output the Korotkoff sound pulse signal SKP when the Korotkoff sound signal exceeds the threshold value TH3. The time at which the initial Korotkoff sound pulse signal SKP is generated is taken as the moment at which the Korotkoff sounds appear for measurement purposes, and the cuff pressure P at this time corresponds to the systolic blood pressure of the person undergoing measurement.

When the MPU 9 accepts the Korotkoff sound pulse signal SKP and recognizes the systolic blood pressure at the decision of step S8, the program proceeds to step S9, at which the cuff pressure P prevailing at this time and read from the cuff pressure detecting unit 7 is displayed on the LED display device 10 as a systolic blood pressure value (SYS). The system waits for the start of the Korotkoff sound pulse signal DKP at step S10. Since the DK-sound filter 25 discriminates (passes) the Korotkoff sound signals at the moment of extinction, it is not particularly important to investigate the Korotkoff sound signal DK at the moment of appearance. Rather, the processing of step S10 is for confirming the start of the Korotkoff sound pulse signals DKP on the premise that extinction of the signals DKP will subsequently be detected. At step S11 the system waits for the end of the Korotkoff sound pulse signals DKP. Since the DK-sound filter 25 discriminates (passes) the Korotkoff sound signals at the moment the Korotkoff sounds vanish, as mentioned above, the moment of extinction is detected in highly reliable fashion. The CMP 26 compares the Korotkoff sound signal DK with the threshold value TH4 and outputs the Korotkoff sound pulse signal DKP when the Korotkoff sound signal DK exceeds the threshold value TH4. Thus, the moment at which the last Korotkoff sound pulse signal DKP is generated is the moment at which the Korotkoff sounds disappear in terms of measurement. The cuff pressure P at such time corresponds to the diastolic blood pressure of the subject undergoing measurement.

When the MPU 9 discriminates that the final Korotkoff sound pulse signal DKP has been received (it is determined that the signal is the last DKP signal when the signal DKP fails to appear within a predetermined period of time), the system proceeds to step S12, at which the cuff pressure prevailing at this time and read from the cuff pressure detecting unit 7 is displayed on the LED display device 10 as the diastolic blood pressure value (DIA). The rapid-discharge valve 14 is opened at step S13 to end measurement.

Measurement Method 2

The characterizing feature of the measurement method 2 is based on separating and extracting a pulse (heartbeat) signal PA from the detected cuff pressure signal P in a cuff pressure detecting unit 7', wherein the amplitude or a change in the amplitude of the extracted pulse signal PA indicates a predetermined property in terms of the systolic blood pressure SYS and diastolic blood pressure DIA of the individual undergoing examination. According to this feature, this property is examined to evaluate the acceptability of the blood pressure measurement results based on the Korotkoff sound signals.

Figure 3:
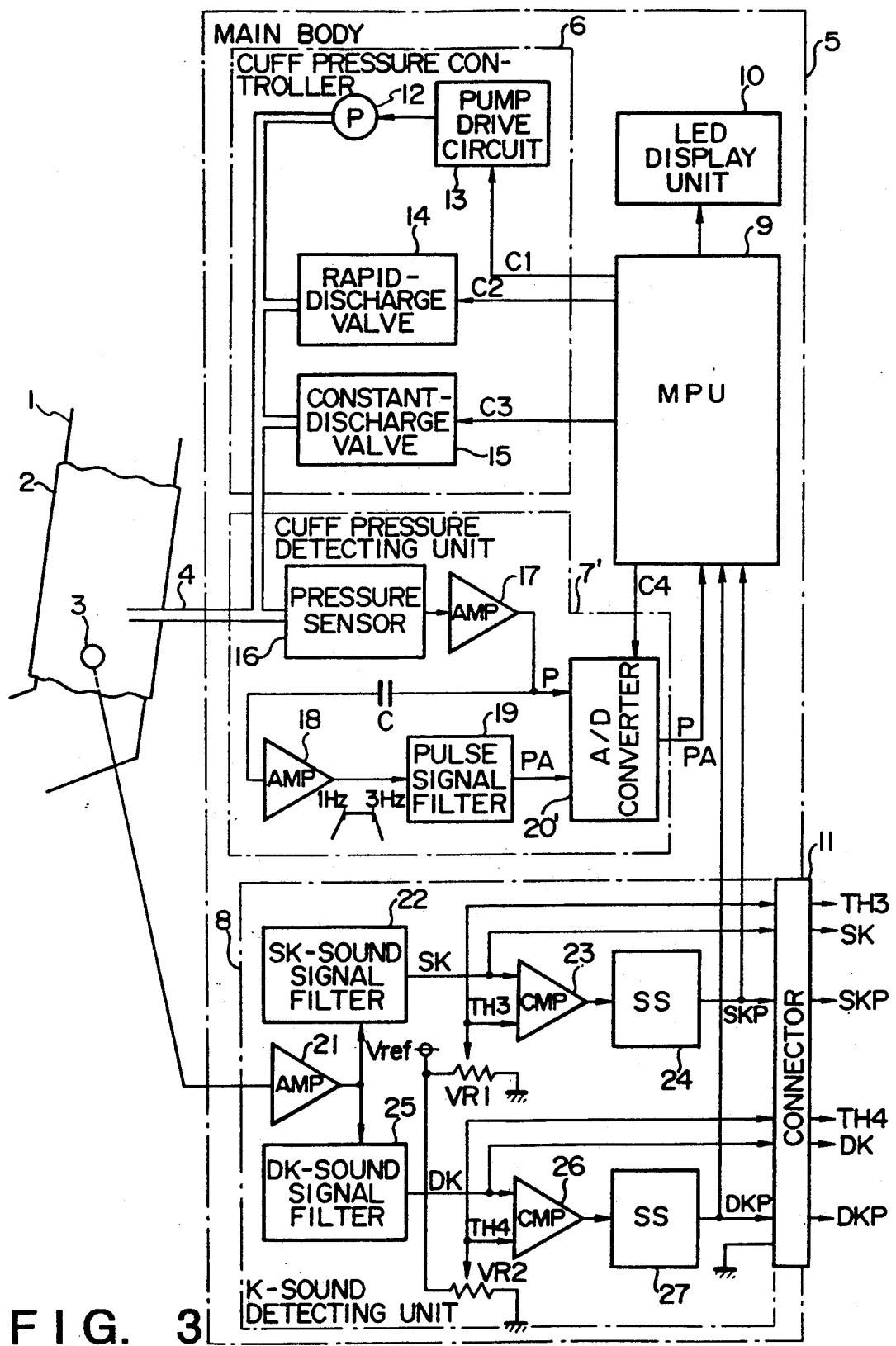
FIG. 3 is a block diagram of an automatic sphygmomanometer using a measurement method 2 according to the present invention.

FIG. 3 is a block diagram showing an automatic sphygmomanometer using measurement method 2 according to the present invention, in which portions similar to those shown in FIG. 1 are designated by like reference characters and are not described again. In FIG. 3, numeral 7' denotes a cuff pressure detecting unit for detecting cuff pressure (cuff pressure and pulse pressure). In the cuff pressure detecting unit 7', numeral 16 denotes a pressure sensor for sensing cuff pressure, 17 an AMP for amplifying the cuff pressure detection signal to output a cuff pressure signal P, C a capacitor for separating and extracting pulse signal components from the cuff pressure signal P, 18 an AMP for amplifying the pulse signal, 19 a pulse signal filter having a predetermined band-pass characteristic (e.g., 1-3 Hz) for outputting the pulse signal PA, and 20' an A/D converter which, in accordance with a control signal C4 from the MPU 9, samples the cuff pressure signal P and pulse signal PA and converts them into digital signals. A pair of variable resistors VR1 and VR2 are used to adjust when appearance and disappearance of pulses SKP and DKP, respectively, are detected, as described below with respect to FIG. 8.

Figure 4:
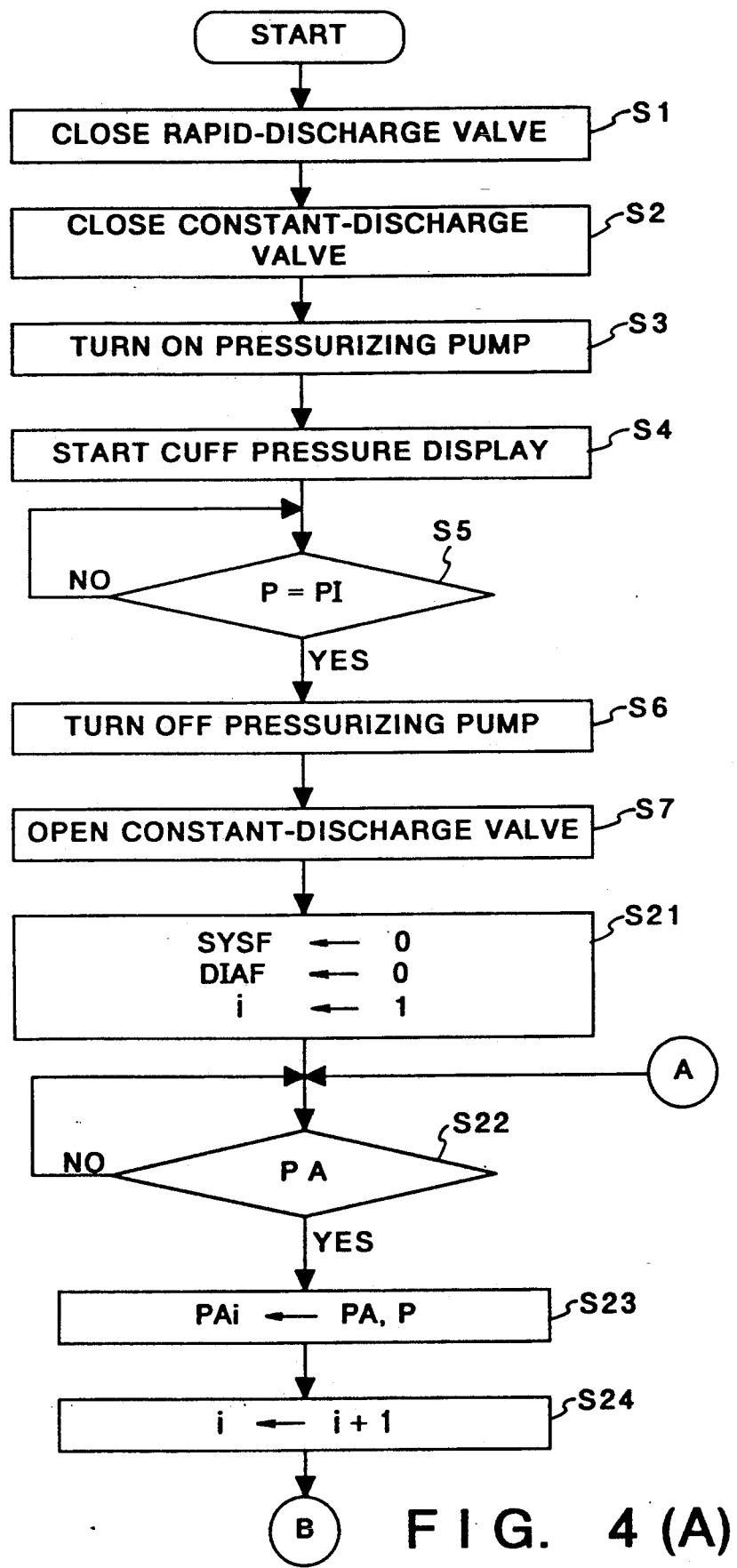
FIGS. 4(A) and 4(B) are flowcharts showing measurement control procedures of the measurement method 2 performed by the MPU 9.
Figure 4:
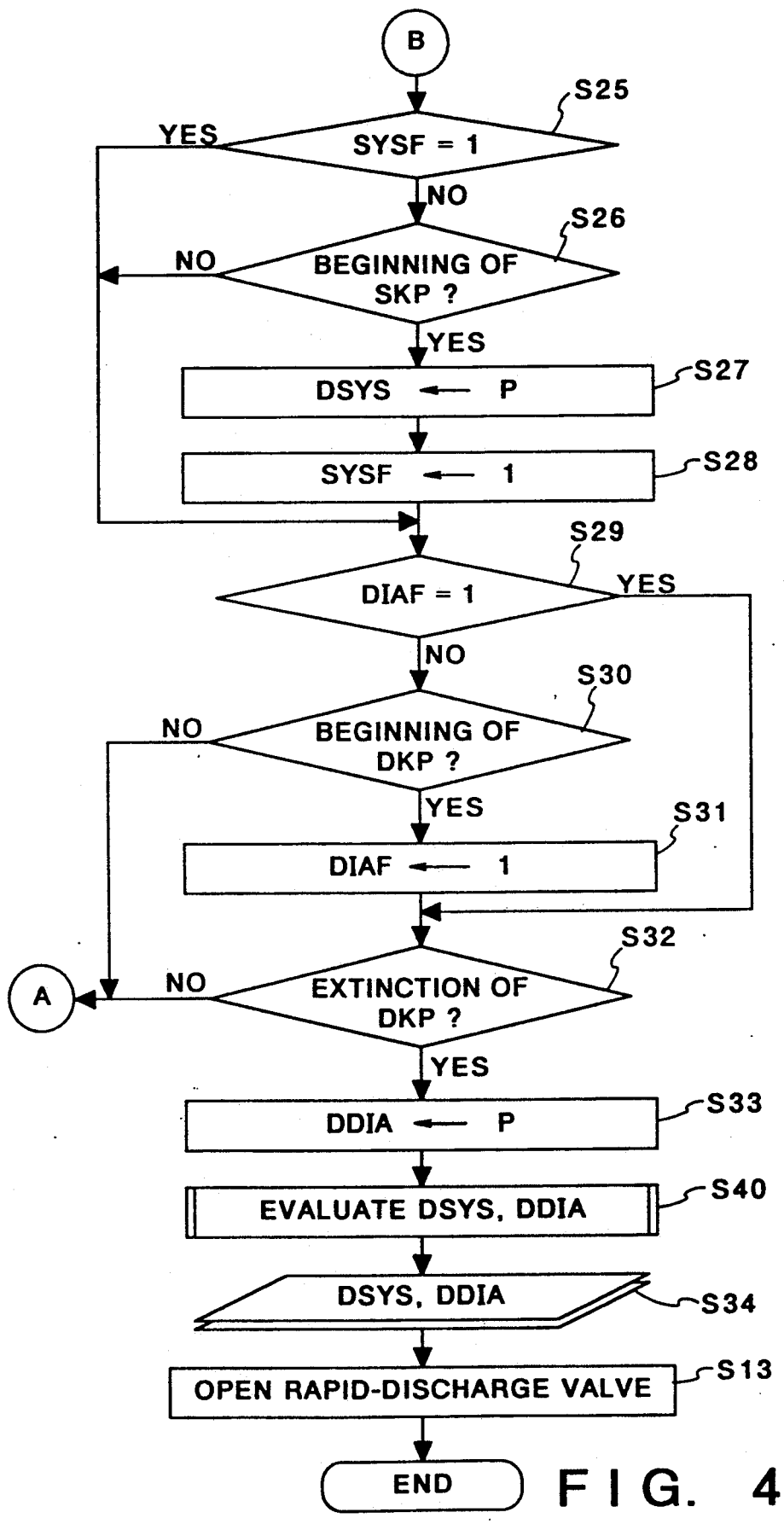
Figure 5A:
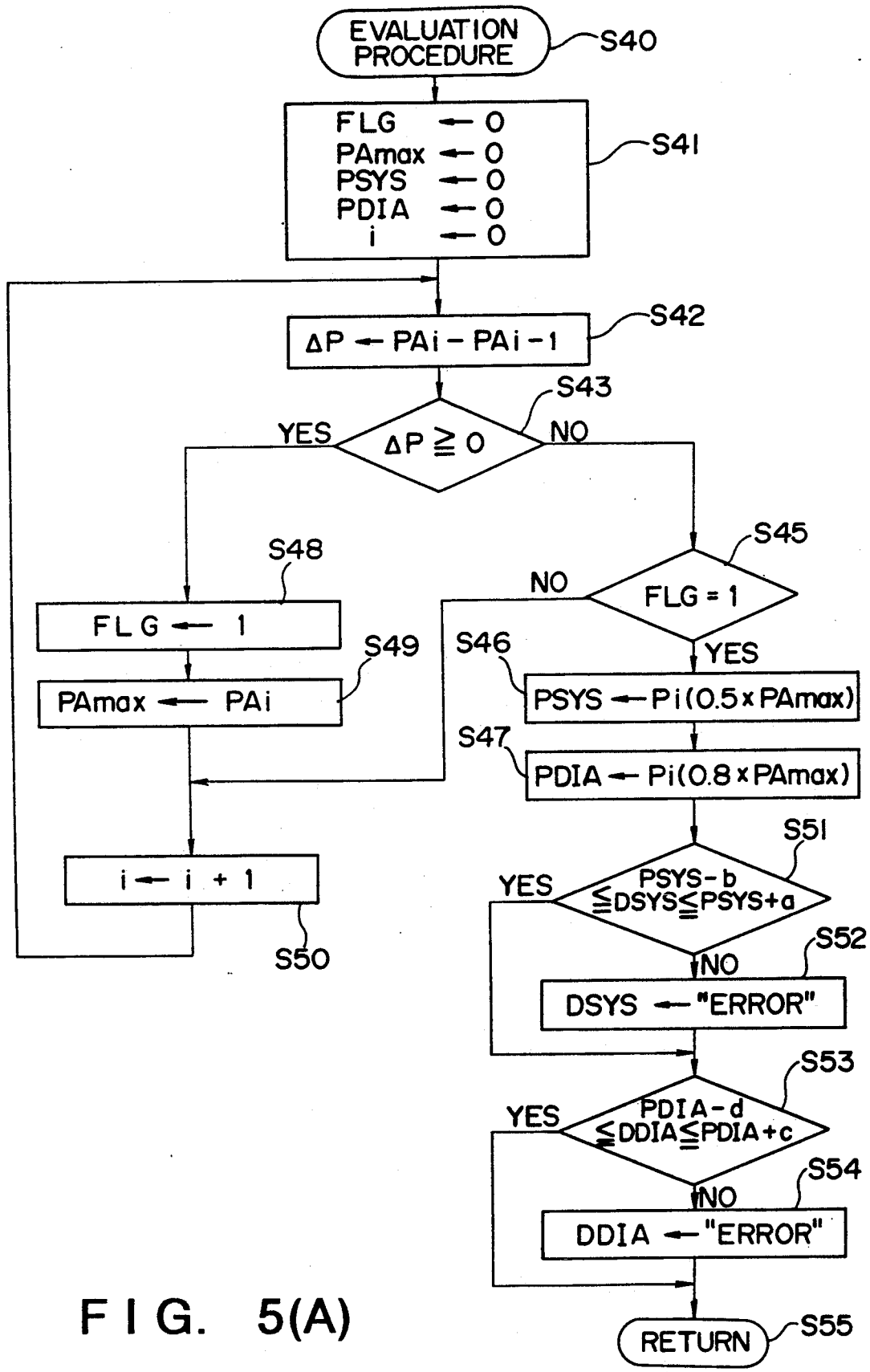
FIG. 5(A) is a flowchart of an evaluation procedure performed by the MPU 9.

FIGS. 4(A), (B) are flowcharts showing measurement control procedures of the measurement method 2 performed by the MPU 9, FIG. 5(A) is a flowchart of an evaluation processing procedure (S40) of FIG. 4(B), and FIG. 6 is an operation timing chart of the measurement method 2. Steps similar to those of FIG. 2 are designated by like step numbers and are not described again.

In FIG. 4(A), the sphygmomanometer enters the blood pressure measurement phase at step S7, whereupon a series of initial settings is made at step S21. Here, SYSF represents a flag which indicates that systolic blood pressure SYS has been determined during the measurement phase, DIAF a flag which indicates that the start of the Korotkoff sound pulse signal DKP has been detected during the measurement phase, and i a general-purpose counter. At step S22 the system waits for the occurrence of the pulse signal PA. When the pulse signal PA is generated, the program proceeds to step S23, at which the amplitude of the pulse signal PA and the cuff pressure P are stored at an address PAi, which is indexed by the counter i, in a memory (not shown) within the MPU 9. The counter i is incremented by +1 at step S24. Thus, in measurement method 2, measurement proceeds along with storage of the amplitude of the pulse signal PA and the cuff pressure P which prevails at such time.

Even in the ischemic state, there is pulsation and pulse pressure (heartbeat) oscillation on the central side of cuff pressure, as shown in FIG. 6. This pulse pressure oscillation (the pulse signal PA) is known to have the following properties: It occurs in advance of the appearance of the Korotkoff sounds and is produced in synchronism with the occurrence of the Korotkoff sounds after these sounds appear. Its amplitude attains a value which is approximately 50% of the maximum amplitude $PA_{max}$ in the vicinity of the systolic blood pressure SYS of the subject undergoing measurement, and subsequently decreases to approximately 80% of the maximum amplitude $PA_{max}$ in the vicinity of the diastolic blood pressure DIA of the subject. This pulse pressure oscillation is known to have the following properties as well: Arterial flow in the upper arm overcomes cuff pressure and is discharged in the vicinity of the systolic blood pre sure SYS of the subject. The volume of the blood vessel under cuff pressure at this time suddenly increases, after which the maximum value PAmax of amplitude is attained owing to the elastic characteristic of the blood vessel wall. Amplitude then decreases sharply. Next, the rate of decrease in amplitude falls below a predetermined value in the vicinity of the diastolic blood pressure DIA of the subject and becomes substantially constant. The pulse signal PA' in FIG. 6 indicates that the A/D-converted pulse signal PA is read by the MPU 9 and that these signals are arrayed in a time series with the amplitude of one signal PA being fixed at the "0" level.

It is determined at step S25 whether SYSF is "1". If it is not "1", this means that the systolic blood pressure SYS has not yet been determined to have occurred. Whether or not the Korotkoff sound pulse signal SKP has begun is investigated at step S26. As long as the signal SKP has not begun, the program returns to step S22 and the next pulse signal PA is awaited. When occurrence of the Korotkoff sounds is eventually determined to have taken place at the decision of step S26, the program proceeds to step S27, where the MPU 9 decides that systolic blood pressure SYS has been attained based on the cuff pressure P at this time and stores the cuff pressure P in display memory DSYS. It is permissible to display the systolic blood pressure SYS provisionally at this time. Next, at step S28, SYSF is set at "1", after which the above-described blood pressure determination process is skipped.

It is determined whether DIAF is "1" at step S29. If it is not "1", this means that the Korotkoff sound pulse signal DKP has not yet begun, and therefore the program proceeds to step S30, where it is determined whether the signal DKP has begun. As long as the signal DKP has not begun, the program returns to step S22 and the next pulse signal PA is awaited. When occurrence of the signal DKP is eventually determined to have takes place at the decision of step S30, the program proceeds to step S31, where DIAF is set at "1". Thereafter the above-described process for verifying the signal DKP is skipped.

Whether or not the Korotkoff sound pulse signal DKP has vanished is investigated at step S32. The conditions which must be satisfied to determine extinction are SYSF=1, DIAF=1, and that after occurrence of the immediately preceding signal DKP, the next signal DKP does not occur within a predetermined period of time [e.g., (60 sec/minimum heartbeat number)×2 beats≈3 sec]. When extinction of the signal DKP is determined to have occurred, the program proceeds to step S33. Here the cuff pressure P which prevailed immediately before the moment of extinction, and which is read out of the cuff pressure detecting unit 7', is decided as being diastolic blood pressure DIA, and this cuff pressure P is stored in the display memory DDIA. It is permissible for the cuff pressure P to be provisionally displayed at this time. Next, at step S40, the systolic blood pressure DSYS and diastolic blood pressure DDIA that have been determined are evaluated [FIG. 5(A) or (B)] in accordance with the properties of the pulse signal PA. Based on the results of the evaluation, systolic blood pressure DSYS and diastolic blood pressure DDIA are displayed at step S34 if appropriate. When inappropriate, the corresponding DSYS or DDIA is displayed in a flashing manner or an "ERROR" display is presented instead.

FIG. 5(A) is a flowchart of the evaluation processing procedure in measurement method 2. In FIG. 5(A), a series of initial settings is made at step S41. Here, FLG represents a flag signifying verification of the fact that the amplitude of the pulse signal PA exhibits an increase, $PA_{max}$ is a register for storing the maximum amplitude $PA_{max}$ of the pulse signal PA, PSYS is a register for storing cuff pressure P which prevails at the moment [moment ② in FIG. 6] the amplitude of the pulse signal PA surpasses approximately 50% of the maximum amplitude $PA_{max}$, PDIA is a register for storing cuff pressure P which prevails at the moment [moment ④ in FIG. 6] the amplitude of the pulse signal PA falls below approximately 80% of the maximum amplitude $PA_{max}$, and i represents a general-purpose counter.

At step S42, the MPU 9 obtains the difference $\Delta P = PA_i - PA_{i-1}$ between consecutive pulse signals. It is permissible to employ running mean values of the respective $PA_i$ and $PA_{i-1}$ in order to raise the anti-noise capability of $\Delta P$ detection. It is determined at step S43 whether $\Delta P \geq 0$ holds. When $\Delta P \geq 0$ holds, this means that the amplitude of the pulse signal PA is increasing and, hence, the program proceeds to step S48, at which FLG is set at "1". At step S49 the value in the register $PA_{max}$ is replaced by a larger value ($Pa_i$). The counter i is incremented by +1 at step S50. If $\Delta P \geq 0$ is found not to hold at the decision of step S43, the program proceeds to step S45, where it is determined whether FLG=1 holds. If FLG=1 does not hold, this indicates that the amplitude of the pulse signal PA has decreased without increasing even once. This is neglected. If FLG=1 holds, this means that the amplitude of the pulse signal PA has made a transition from increasing to decreasing. As a result, $PA_{max}$ in FIG. 6 is detected.

The cuff pressure P at time ③ is known as mean blood pressure. The flow proceeds to step S46, where the systolic blood pressure is stored in PSYS. More specifically, the counter i is decremented by −1, PA(i) is read out successively, and the cuff pressure P(i), which prevails at the moment the amplitude of the pulse signal becomes 50% of the maximum amplitude $PA_{max}$, is read out and stored in PSYS. The diastolic blood pressure is stored in the PDIA at step S47. More specifically, the counter i is incremented by +1 from the instant of $PA_{max}$, PA(i) is read out successively, and the cuff pressure p(i), which prevails at the moment the amplitude of the pulse signal becomes 80% of the maximum amplitude $PA_{max}$, is read out and stored in PDIA. It is determined at step S51 whether the systolic blood pressure DSYS decided at step S27 in FIG. 4(B) lies within the following limits: $(PSYS - b) \leq DSYS \leq (PSYS + a)$. Here, a is 10 mmHg and b is 10 mmHg, by way of example. If it is found at step S51 that the systolic blood pressure does not lie within the aforementioned limits, the program proceeds to step S52, at which "ERROR" is written in the register DSYS. If the systolic blood pressure does lie within the aforementioned limits, then the processing of step S52 is skipped. It is determined at step S53 whether the diastolic blood pressure DDIA decided at step S33 in FIG. 4(B) lies within the following limits: $(PDIA - d) \leq DDIA \leq (PDIA + c)$. Here, c is 10 mmHg and d is 10 mmHg, by way of example. If it is found that the diastolic blood pressure does not lie within the aforementioned limits, the program proceeds to step S54, at which "ERROR" is written in the register DDIA. If the diastolic blood pressure does lie within the aforementioned limits, then the processing of step S54 is skipped.

FIG. 5(B) is a flowchart of another evaluation processing procedure in measurement method 2. Steps similar to those shown in FIG. 5(A) are designated by like step numbers and are not described again. In FIG. 5(B), a series of initial settings is made at step S61. Here, PSYS is a register for storing cuff pressure P which prevails at a time [time ①−② in FIG. 6] at which the amplitudes of consecutive pulse signals PA rise suddenly to surpass a predetermined value q, PDIA is a register for storing cuff pressure P which prevails at a time [time ④−⑤ in FIG. 6] at which the rate of the decrease in the amplitudes of consecutive pulse signals PA falls below a predetermined value k after the MPU 9 has marked the maximum amplitude $PA_{max}$ [time ③ in FIG. 6], and i represents a general-purpose counter.

It is determined at step S43 whether $\Delta P \geq 0$ holds. When $\Delta P \geq 0$ holds, it is determined a step S65 whether $\Delta P \geq q$ holds. If $\Delta P \geq q$ holds, this means that the amplitudes of consecutive pulse signals PA have risen sharply above the predetermined value q and, hence, the program proceeds to step S66, at which the cuff pressure $P_i$ prevailing at this time is stored in the register PSYS. If $\Delta P \geq q$ does not hold, the step S66 is skipped. When $\Delta P \geq 0$ is found not to hold at the decision of step S43, this means that the amplitude of the pulse signal PA is decreasing and, hence, the program proceeds to step S67, at which it is determined whether $|\Delta P| \leq k$ holds. In this case, it is preferred that whether or not $|\Delta P| \leq k$ holds be investigated after verifying that the amplitude exhibits a rate of decrease greater than a predetermined value. If $|\Delta P| \leq k$ holds, this means that the amplitudes of consecutive pulse signals PA have made a transition from a sharply decreasing state to a slowly decreasing state. Therefore, the program proceeds to step S68, at which the immediately preceding cuff pressure $P_{i-1}$ is stored in the register PDIA. If $|\Delta P| \leq k$ does not hold, step S68 is skipped. It is determined at step S69 whether the count in counter i is M, where M represents the total number of pulse signals PA stored during blood pressure measurement. If i=M does not hold, the counter i is incremented by +1 at step S50 and the program returns to step S42. If i=M does hold, the program proceeds to step S51.

In accordance with measurement method 2 set forth above, all of the pulse signals PA and cuff pressures P are stored as measurement progresses, after which the nature of the stored data is investigated. However, the invention is not limited to this arrangement. For example, it is possible to adopt an arrangement in which the evaluation processing of FIG. 5(A) or 5(B) is performed in parallel with the processing of FIGS. 4(A) and 4(B). In such case, information relating to characteristic points (the vicinity of the systolic blood pressure SYS and the vicinity of the diastolic blood pressure DIA) would be examined based on the stored pulse signals PA at a moment in mid-course that the necessary pulse signals PA and cuff pressures P are stored. Then, after the corresponding cuff pressures P are specified and stored, the pulse signals PA and cuff pressures P that are no longer necessary would be cleared from memory each time, thereby making it possible to conserve memory.

Adjustment of Automatic Sphygmomanometer

It is preferred from a medical point of view that the display of systolic and diastolic blood pressures in this type of automatic sphygmomanometer agree with the results of a conventional measurement method, performed by a physician, using points at which Korotkoff sounds are found to appear and disappear, or some other criteria, as a reference. To this end, the automatic sphygmomanometers employing the foregoing two measurement methods are capable of being externally adjusted with ease at the time of use.

Figure 8:
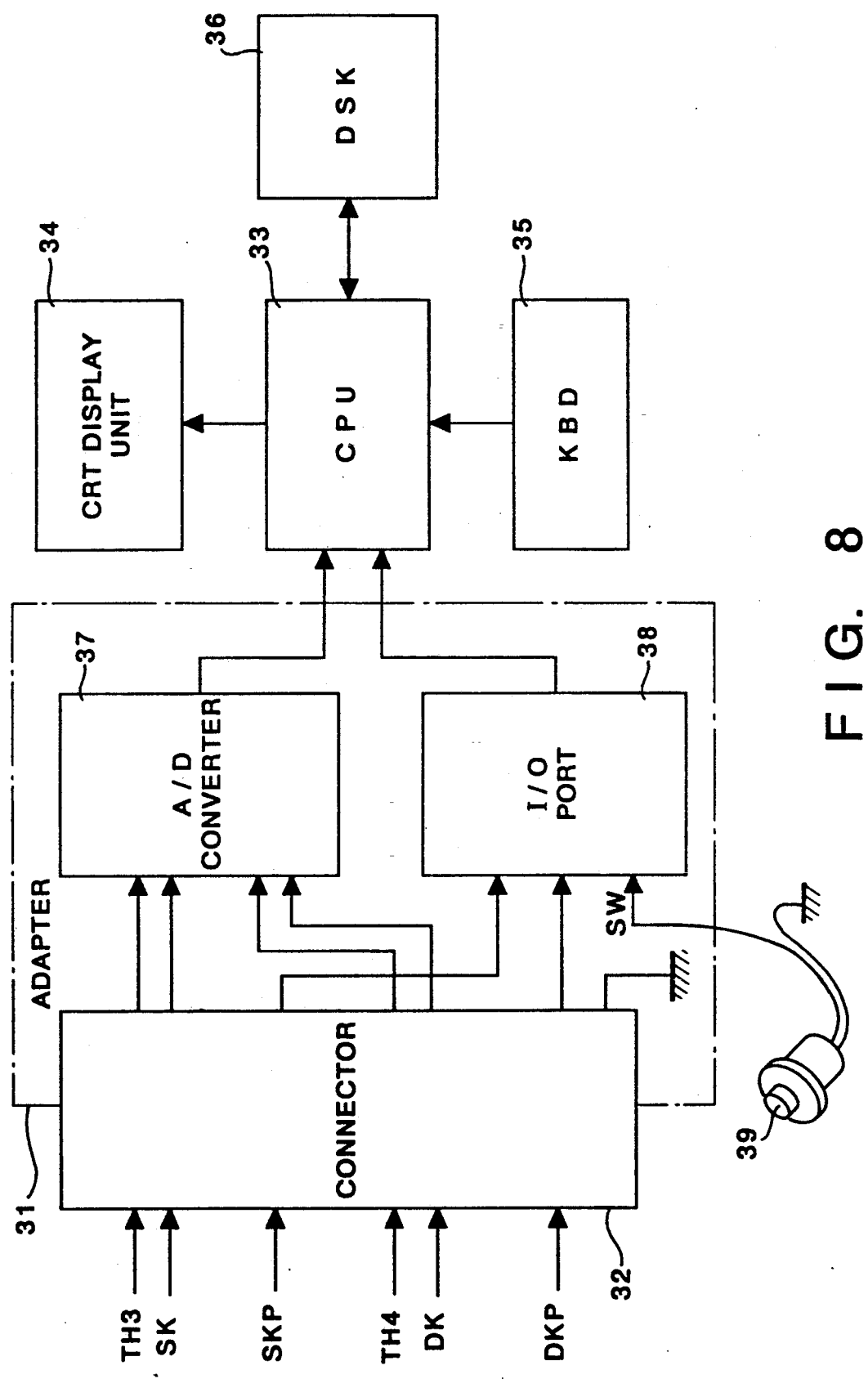
FIG. 8 is a block diagram showing an adjustment system of an automatic sphygmomanometer according to the embodiment.

FIG. 8 is a block diagram of a system for adjusting the automatic sphygmomanometer of the embodiment. In FIG. 8, numeral 31 denotes an adapter for extracting a predetermined signal from the automatic sphygmomanometer, 32 a connector connected to the automatic sphygmomanometer, 33 a central processing unit (CPU) for processing data necessary for adjustment of the automatic sphygmomanometer, 34 a CRT display unit for displaying the data necessary for adjustment of the automatic sphygmomanometer, 35 a keyboard (KBD) for giving instructions to the CPU 33, 36 a magnetic disk device (DSK) for storing the data extracted from the automatic sphygmomanometer, and 39 a switch operated as by a physician at the moment appearance and disappearance of Korotkoff sounds is determined by auscultation.

In the adapter 31, numeral 37 denotes an A/D converter for converting the various analog signals TH3, SK, TH4, DK within the automatic sphygmomanometer into digital signals which are then outputted to the CPU 33. Numeral 38 denotes an I/O port to which are applied the Korotkoff sound pulse signals SKP, DKP within the automatic sphygmomanometer as well as a signal from the switch 39 externally operated by the listener (physician, etc.), and from which these signals are outputted to the CPU 33. As measurement proceeds, the CPU 33 arranges these items of input data in a time series and stores them temporarily in the DSK 36. At the same time, the switch 39 is pressed as by a physician at the moments the Korotkoff sounds are perceived to appear and disappear, using the auscultation method or the like, as measurement proceeds. The signal SW (at times ②″ and ④″) in FIG. 6 illustrates this relationship. After measurement of blood pressure, the CPU 33 reads these items of data out of the DSK 36 and displays them on the CRT display unit 34. The method of displaying these data is from signal SK to signal SW in FIG. 6, by way of example. As a result, a physician or the like is capable of readily evaluating, based on the data presented on the CRT display, whether the moment ②′ at which appearance of the Korotkoff sounds is detected by the automatic sphygmomanometer agrees with the moment ②″ at which appearance of the Korotkoff sounds is perceived by auscultation. If the two agree, the level of the signal TH3 is appropriate. If the two do not agree, then VR1 is adjusted externally, thereby making it possible to readily adjust the moment at which appearance of the SKP signal is detected. In another option, it can be arranged to adjust the gain (signal amplitude) of the SK-sound signal filter 22. A further option is to adopt an arrangement in which the filter constant (the band-pass characteristic or the like) of the SK-sound signal filter 22 is adjusted. Similarly, the operator is capable of readily evaluating whether the moment ④′ at which disappearance of the Korotkoff sounds is detected by the automatic sphygmomanometer agrees with the moment ④″ at which disappearance of the Korotkoff sounds is perceived by auscultation. If the two agree, the level of the signal TH4 is appropriate. If the two do not agree, then VR2 is externally adjusted so that the moment at which disappearance of the signal DKP is detected can be readily adjusted. In another option, it can be arranged to adjust the gain (signal amplitude) of the DK-sound signal filter 25. A further option is to adopt an arrangement in which the filter constant (the band-pass characteristic or the like) of the DK-sound signal filter 25 is adjusted. Thus, adjustment of the moment at which the Korotkoff sounds appear and adjustment of the moment at which the Korotkoff sounds disappear can be performed separately. As a result, more precise, accurate adjustment can be carried out.

Measurement Method 3

It is obvious that the present invention can be applied also to measurement of blood pressure during inflation of the cuff. Measurement method 3 is related to such measurement of blood pressure during cuff inflation.

Figure 9:
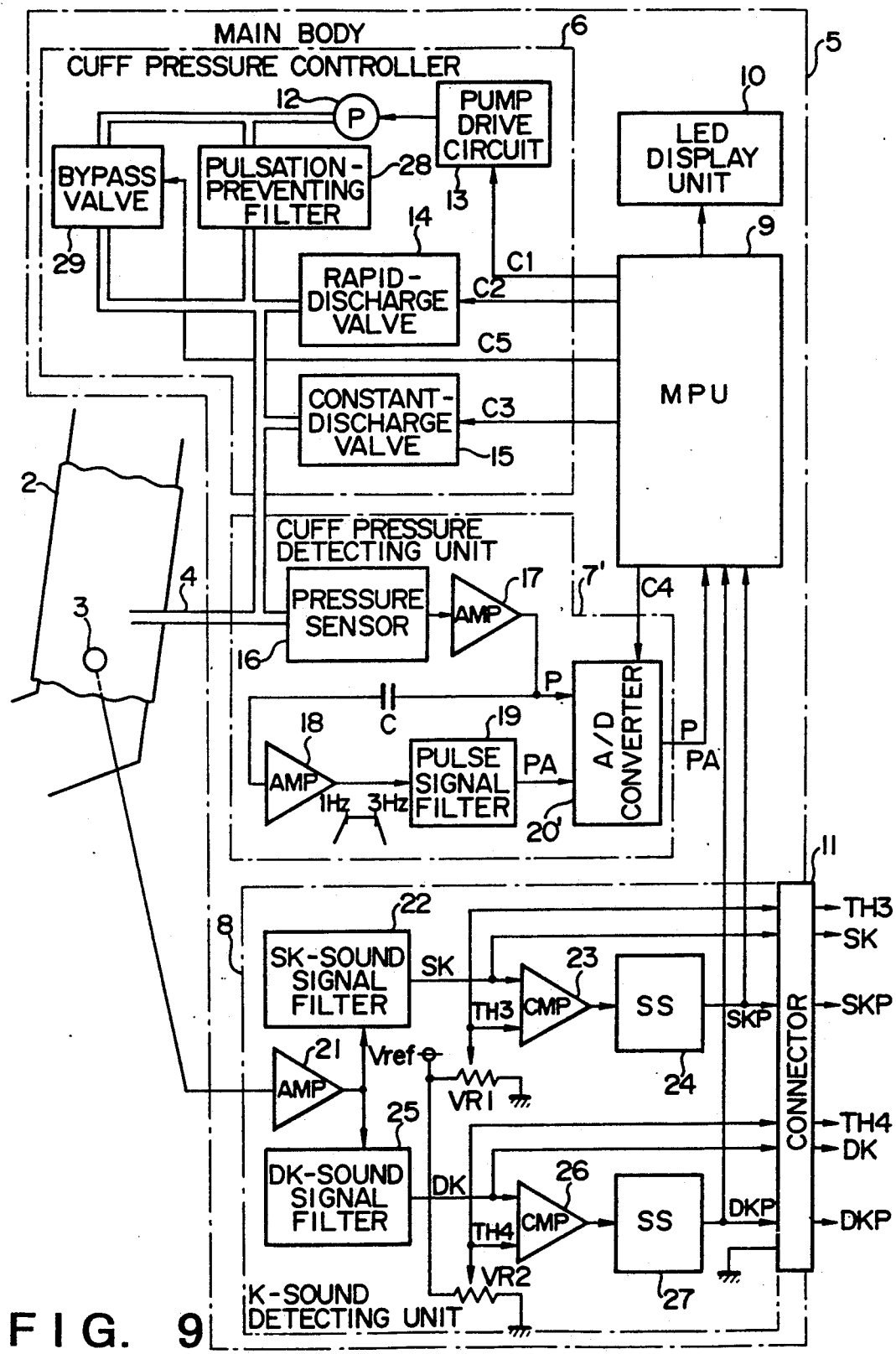
FIG. 9 is a block diagram of an automatic sphygmomanometer using a measurement method 3 according to the present invention.

FIG. 9 is a block diagram showing an automatic sphygmomanometer using measurement method 3 according to the present invention, in which portions similar to those shown in FIGS. 1 and 3 are designated by like reference characters and are not described again. In FIG. 9, numeral 28 denotes a pulsation-preventing filter (low-pass filter) for cutting out pumping sounds and the like during cuff inflation. Numeral 29 denotes a bypass valve for bypassing the flow path of the pulsation-preventing filter. The pump driving circuit 13 is capable of controlling the inflating rate of the cuff 2.

Figure 10:
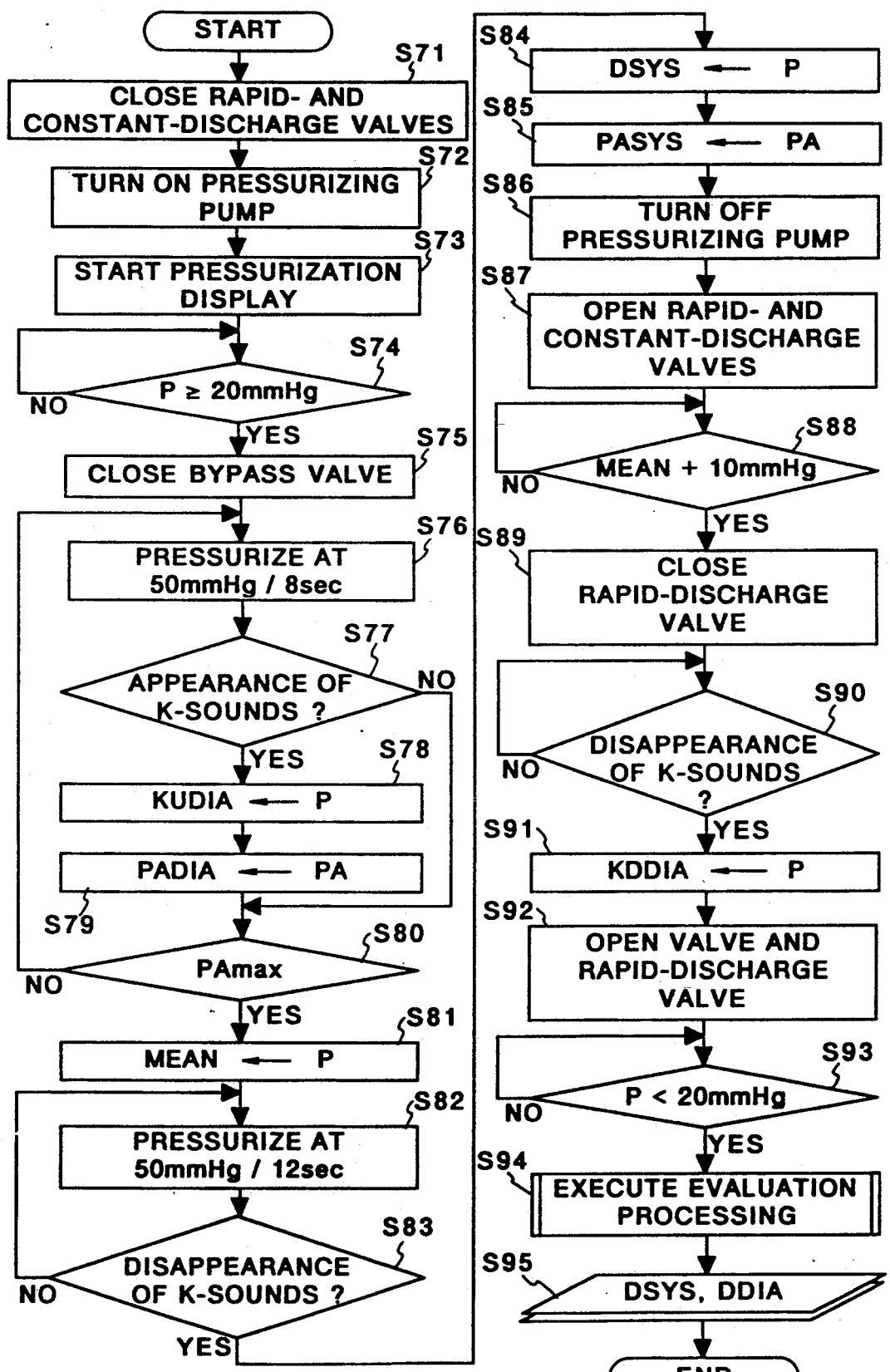
FIG. 10 is a flowchart showing a measurement control procedure of the measurement method 3 performed by the MPU 9.
Figure 11:
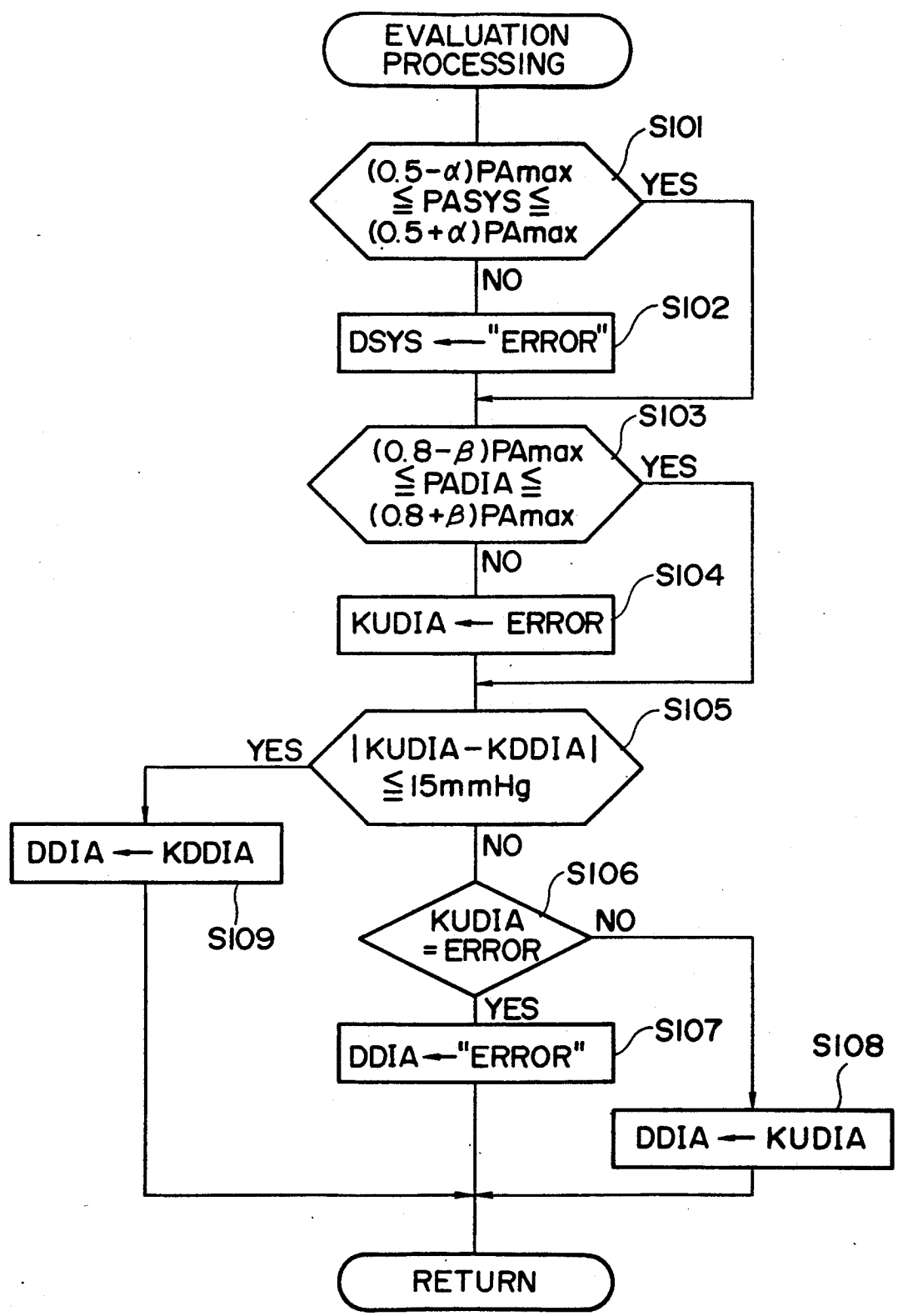
FIG. 11 is a flowchart of an evaluation procedure performed by the MPU 9.
Figure 12:
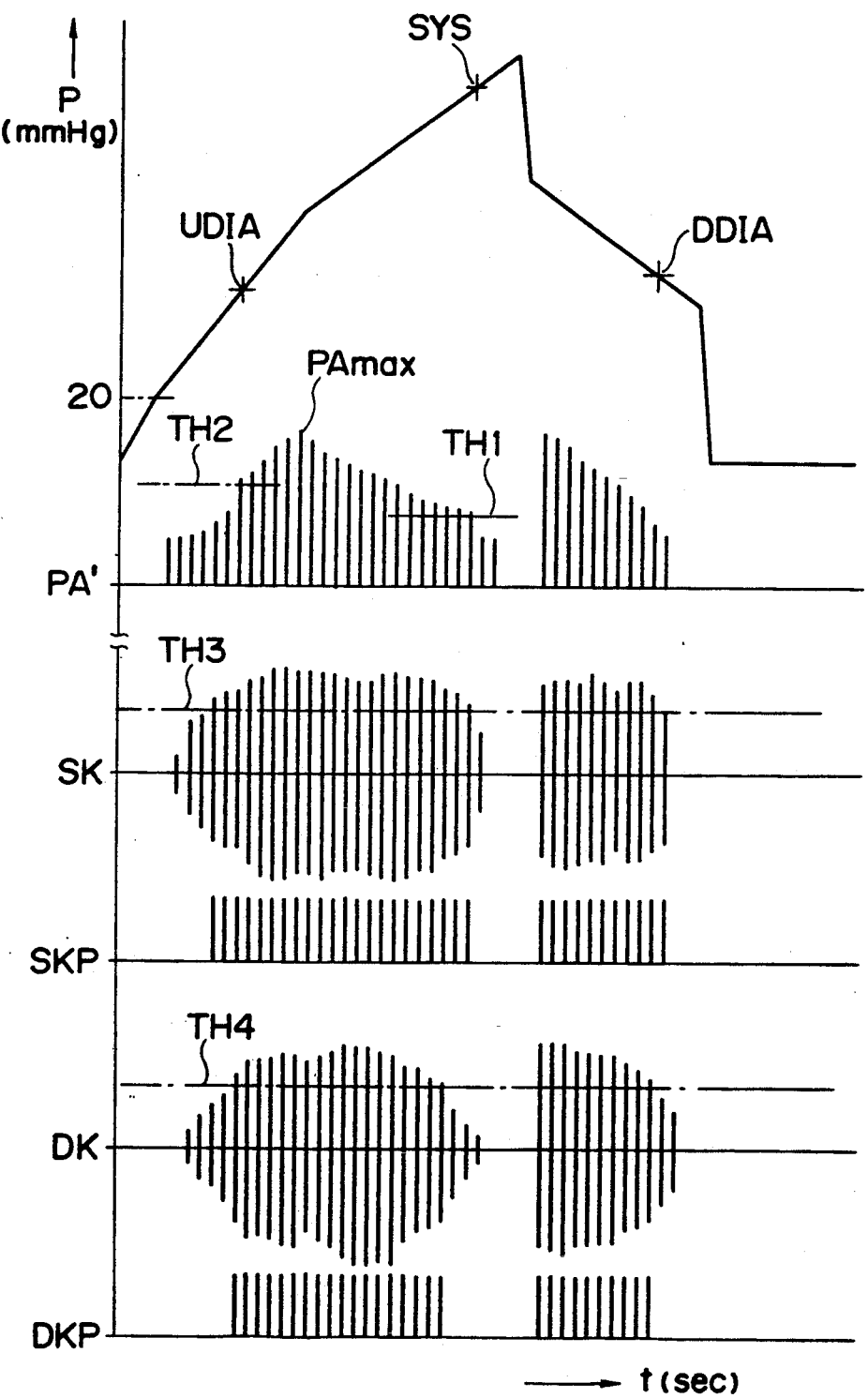
FIG. 12 is an operation timing chart of the automatic sphygmomanometer using the measurement method 3.

FIG. 10 is a flowchart showing a measurement control procedure using measurement method 3 performed by the MPU 9, and FIG. 12 is an operation timing chart of the automatic sphygmomanometer using measurement method 3. In FIG. 10, the rapid-discharge valve 14 and constant-discharge valve 15 are closed at step S71. The inflating pump 12 is turned on at step S72, and display of cuff pressure is started at step S73. The system waits for cuff pressure P to attain a value of 20 mmHg at step S74. When 20 mmHg is attained, the bypass valve 29 is closed at step S75. As a result, air is supplied via the pulsation-preventing filter 28. The inflating rate of the cuff 2 is controlled to be 50 mmHg per 8 sec at step S76. Measurement of diastolic blood pressure UDIA during inflation is for preparatory purposes and is performed comparatively roughly. It is determined at step S77 whether the K-sounds have appeared (start of DKP). If the K-sounds have appeared, the cuff pressure P prevailing at this instance is stored in register KUDIA at step S78. This is diastolic blood pressure UDIA detected during cuff inflation. Pulse amplitude PA prevailing at this instant is stored in register PADIA at step S79. PADIA is pulse amplitude at the moment diastolic blood pressure UDIA is detected. If the K-sounds do not appear at the decision of step S77, steps S78, S79 are skipped. The maximum value $PA_{max}$ of pulse amplitude is detected at step S80. As long as the amplitude is not $PA_{max}$, the program returns to step S76. When $PA_{max}$ is eventually detected, the cuff pressure P prevailing at this instant is stored in a register MEAN at step S81. MEAN represents mean blood pressure. The rate of inflation of cuff 2 is controlled to 50 mmHg per 12 sec at step S82. Since measurement of systolic blood pressure USYS during inflation is performed only once, measurement precision is raised. It is determined at step S83 whether the K-sounds have vanished (SKP extinction). The program returns to step S82 as long as the K-sounds do not vanish. When the K-sounds eventually disappear, the cuff pressure P prevailing at this instant is stored in register DSYS at step S84. DSYS is systolic blood pressure SYS detected during cuff inflation. Pulse amplitude PA prevailing at this instant is stored in register PASYS at step S85. PASYS is pulse amplitude at the moment systolic blood pressure DSYS is detected. The inflating pump 12 is turned OFF at step S86, and the rapid-discharge valve 14 and constant-discharge valve 15 are opened at step S87. Cuff pressure declines rapidly as a result. At step S88, the system waits for the cuff pressure to decline to MEAN (mean blood pressure)+10 mmHg. When the cuff pressure eventually falls to MEAN+10 mmHg, only the rapid-discharge valve 14 is closed at step S89. The system waits for the K-sounds (DKP) to vanish at step S90. When the K-sounds vanish, cuff pressure P at this instant (cuff pressure corresponding to the last K-sound which prevailed before extinction) is stored in register KDDIA at step S91. KDDIA represents diastolic blood pressure DDIA detected during cuff deflation. The bypass valve 29 and rapid-discharge valve 14 are opened at step S92. The system waits for cuff pressure P to fall below 20 mmHg at step S93. When the cuff pressure P falls below 20 mmHg, the evaluation processing of FIG. 11 is carried out at step S94. Information indicative of the systolic blood pressure DSYS and diastolic blood pressure DDIA of the subject undergoing measurement is displayed at step S95.

FIG. 11 is a flowchart of an evaluation procedure performed by the MPU 9. It is determined at step S101 whether $[(0.5-\alpha)\times PA_{max}] \leq PASYS \leq [(0.5+\alpha)\times PA_{max}]$ holds. If PASYS lies within the abovementioned limits, it is decided that the systolic blood pressure DSYS detected at step S84 is correct. When PASYS does not lie within the abovementioned limits, the "ERROR" message is stored in the register DSYS at step S102. It is determined at step S103 whether $[(0.8-\beta)PA_{max}] \leq PADIA \leq [(0.8+\beta)\times PA_{max}]$ holds. If PASYS lies within the abovementioned limits, it is assumed for the time being that the diastolic blood pressure KUDIA detected at step S78 is correct. When PASYS does not lie within the abovementioned limits, the ERROR information (e.g., FF) is stored in the register KUDIA at step S104. It is determined at step S105 whether $|KUDIA - KKDIA| \leq 15$ mmHg holds. If the decision is YES, the contents of KDDIA detected at step S91 are stored in the register DDIA at step S109. The display of diastolic blood pressure takes priority over the results of measurement obtained at the time of cuff deflation. If the decision at step S105 is NO, then it is determined at step S106 whether KUDIA=ERROR information holds. If KUDIA=ERROR information does hold, the "ERROR" message is stored in DDIA at step S107. If KUDIA=ERROR information does not hold, then the contents of KUDIA are stored in DDIA at step S108. Since KUDIA has passed through the evaluation of step S103, it is possible to employ this in the display of diastolic blood pressure.

In each of the foregoing measurement methods, information relating to determination of systolic blood pressure and diastolic blood pressure is displayed on the LED display unit 10. However, the present invention is not limited to this arrangement, for it is permissible to output this information by a voice track or the like.

Further, in each of the foregoing measurement methods, the arrangement is such that the signals extracted via the connector 11 are processed via the CPU 33. However, the invention is not limited to this arrangement. An example of a simpler arrangement would be one in which these signals are directly compared and observed on the CRT unit or the like by using a predetermined trigger, thereby making it possible to make a comparison with the results of blood pressure measurement perceived by auscultation. Alternatively, an arrangement can be adopted in which predetermined sounds are produced directly in speaker or the like by the signals SKP, DKP, etc. This arrangement also will make it possible to effect a comparison with the results of blood pressure measurement perceived by auscultation.

In accordance with the present invention as described above, a range in which the systolic blood pressure of a subject undergoing measurement is capable of residing and a range in which the diastolic blood pressure of the subject is capable of residing are set based on the transition of pulse signal components of a cuff pressure signal. As a result, it is possible to effectively monitor misrecognition due to oscillatory noise as well as misrecognition due to a shift in sensor position or sensor failure. This makes it possible to correctly judge whether measurement has been performed correctly.

Further, in accordance with the present invention, the automatic sphygmomanometer is equipped with signal extracting means for externally extracting Korotkoff sound signals or signals indicative of predetermined threshold values, and adjusting means for performing adjustment based on these signals. As a result, it is possible to easily monitor measurement condition, and to easily calibrate the measurement condition at use.

In accordance with the present invention, a comparison can readily be made with measurement results based on auscultation or some other criteria. This makes it possible for the automatic sphygmomanometer to be readily applied for a variety of uses and purposes.

What is claimed is:

1. An automatic sphygmomanometer for measuring blood pressure of a subject based on Korotkoff sound signals generated during pressurization using a cuff, comprising:

cuff pressure detecting means for detecting cuff pressure and outputting a cuff pressure signal including a pulse signal component;

Korotkoff sound detecting means for detecting Korotkoff sounds and outputting Korotkoff sound signals;

Korotkoff sound signal processing means for performing amplifying and filtering processing based on the Korotkoff sound signals to produce processed Korotkoff sound signals and for comparing the processed Korotkoff sound signals with a predetermined threshold value to obtain extracted Korotkoff sound signals which exceed the predetermined threshold value;

blood pressure determining means for determining systolic blood pressure and diastolic blood pressure based on the extracted Korotkoff sound signals;

range setting means for setting ranges based on a transition of the pulse signal component of the cuff pressure signal, the ranges including a range in which systolic blood pressure of the subject is capable of residing and a range in which diastolic blood pressure of the subject is capable of residing;

evaluating means for providing an indication of whether the systolic and diastolic blood pressures determined by said blood pressure determining means reside in the ranges set by said range setting means; and display means for displaying information indicative of the systolic and diastolic blood pressures determined by said blood pressure determining means and the indication made by said evaluating means.

2. An automatic sphygmomanometer according to claim 1, wherein said range setting means sets, as the range in which the systolic blood pressure is capable of residing, a first predetermined range which includes the cuff pressure that prevails when a first pulse signal, equivalent to a maximum amplitude of the pulse signal component multiplied by n ($0 < n < 1$), appears at one of a beginning and an end of a measurement phase, and sets, as the range in which the diastolic blood pressure is capable of residing, a second predetermined range which includes the cuff pressure that prevails when a second pulse signal, equivalent to the maximum amplitude of the pulse signal component multiplied by m ($0 < m < 1$), appears at one of the end and the beginning of the measurement phase, these settings being made in conformity with one of a cuff deflation measurement sequence and a cuff inflation measurement sequence.

3. An automatic sphygmomanometer according to claim 1, wherein the range setting means sets, as the range in which the systolic blood pressure is capable of residing, a first predetermined range which includes the cuff pressure that prevails when signal amplitudes of consecutive pulse signal components exhibit one of more than a first predetermined rate of increase at a beginning of a measurement phase and less than a first predetermined rate of decrease at an end of the measurement phase, and sets, as the range in which the diastolic blood pressure is capable of residing, a second predetermined range which includes the cuff pressure that prevails when the signal amplitudes of the consecutive pulse signal components exhibit one of less than a second predetermined rate of decrease at the end of the measurement phase and more than a second predetermined rate of increase at the beginning of the measurement phase, these settings being made in conformity with a cuff deflation measurement sequence or a cuff inflation measurement sequence.

4. An automatic sphygmomanometer according to claim 1, wherein said display means adds flashing information to the information indicative of either of the systolic and diastolic blood pressures determined to be unacceptable by said evaluating means.

5. An automatic sphygmomanometer according to claim 1, wherein said display means displays an error message instead of information indicative of either of the systolic and diastolic blood pressures determined to be unacceptable by said evaluating means.

6. An automatic sphygmomanometer according to claim 1, further comprising:

signal extracting means for externally extracting the processed Korotkoff sound signals and a signal indicative of the predetermined threshold value; and adjusting means for externally adjusting the predetermined threshold value and one of the amplitude of the processed Korotkoff sound signals and a filter constant.

7. An automatic sphygmomanometer according to claim 1, wherein said Korotkoff sound signal processing means comprises:

first filter means for passing the Korotkoff sound signals in a first region including an expected systolic blood pressure to produce first processed Korotkoff sound signals;

fist comparator means for comparing the first processed Korotkoff sound signals with a first predetermined threshold value to produce first extracted Korotkoff sound signals;

second filter means for passing the Korotkoff sound signals in a second region including an expected diastolic blood pressure to produce second processed Korotkoff sound signals; and second comparator means for comparing the second processed Korotkoff sound signals with a second predetermined threshold value to produce second extracted Korotkoff sound signals.

8. An automatic sphygmomanometer according to claim 7, wherein said blood pressure determining means determines the systolic blood pressure to be the blood pressure which prevails when the first extracted Korotkoff sound signals disappear, and determines the diastolic blood pressure to be the blood pressure which prevails when the second extracted Korotkoff sound signals appear, both determinations being made in conformity with a cuff deflation measurement.

9. An automatic sphygmomanometer according to claim 7, wherein said blood pressure determining means determines the systolic blood pressure to be the blood pressure which prevails when the first extracted Korotkoff sound signals disappear, and determines the diastolic blood pressure to be the blood pressure which prevails when the second extracted Korotkoff sound signals appear, both determinations being made in conformity with a cuff inflation measurement.

* * * * *